(12) United States Patent
Weng et al.

(10) Patent No.: US 6,719,694 B2
(45) Date of Patent: Apr. 13, 2004

(54) ULTRASOUND TRANSDUCERS FOR IMAGING AND THERAPY

(75) Inventors: Lee Weng, Bellevue, WA (US); David M. Perozek, Mercer Island, WA (US); Jimin Zhang, Bellevue, WA (US)

(73) Assignee: Therus Corporation, Seattle, WA (US)

( * ) Notice: Subject to any disclaimer, the term of this patent is extended or adjusted under 35 U.S.C. 154(b) by 284 days.

(21) Appl. No.: 09/747,310

(22) Filed: Dec. 22, 2000

(65) Prior Publication Data

US 2001/0031922 A1 Oct. 18, 2001

Related U.S. Application Data

(60) Provisional application No. 60/171,703, filed on Dec. 23, 1999.

(51) Int. Cl.⁷ ............................................. A61B 8/00
(52) U.S. Cl. ................. 600/439; 600/437; 600/444; 600/459; 601/2; 310/336
(58) Field of Search ........................ 600/439, 444, 600/459; 601/2; 310/336

(56) References Cited

U.S. PATENT DOCUMENTS

| | | | |
|---|---|---|---|
| 4,484,569 A | 11/1984 | Driller et al. | 128/660 |
| 4,757,820 A | 7/1988 | Itoh | 128/660 |
| 4,938,216 A | 7/1990 | Lele | 128/399 |
| 4,938,217 A | 7/1990 | Lele | 128/399 |
| 4,957,099 A | 9/1990 | Hassler | 128/660 |
| 5,243,988 A | 9/1993 | Sieben et al. | 128/662.06 |
| 5,558,092 A | * 9/1996 | Unger et al. | 600/439 |
| 5,738,635 A | 4/1998 | Chapelon et al. | 601/2 |
| 5,823,962 A | * 10/1998 | Schaetzle et al. | 600/439 |
| 6,050,943 A | 4/2000 | Slayton et al. | 600/439 |
| 6,182,341 B1 | 2/2001 | Talbot et al. | 29/25.35 |

OTHER PUBLICATIONS ter Haar, G., "Ultrasound Focal Beam Surgery," *Ultrasound in Medicine and Biology*, 1995, vol. 21, No. 9, pp. 1089–1100.

Sanghvi, N.T. and Hawes, R.H., "High–Intensity Focused Ultrasound," *Experimental and Investigational Endoscopy*, Apr. 1994, vol. 4, No. 2, pp. 383–395.

Hutchinson, E.B. and Hynynen, K., "Intracavitary Ultrasound Phased Arrays for Noninvasive Prostate Surgery," *IEEE Transactions on Ultrasonics, Ferroelectrics, and Frequency Control*, Nov. 1996, vol. 43, No. 6, pp. 1032–1042.

Barthe, P.G. and Slayton, M.H., "Efficient Wideband Linear Arrays for Imaging and Therapy," *IEEE Ultrasonics Symposium*, 1999, pp. 1249–1252.

* cited by examiner

*Primary Examiner*—Dennis W. Ruhl
*Assistant Examiner*—Jeoyuh Lin

(57) ABSTRACT

Ultrasound applicators able to both image a treatment site and administer ultrasound therapy include an array of transducer elements that can be focused. In several embodiments, an electronically phased array is used for controlling the focal point of an ultrasound beam. The ultrasound beam produced thereby can also be electronically steered. To reduce the quality factor or Q of the array when the array is used for imaging, an electronic switch is selectively closed, placing a resistance in parallel with each of the array elements. A flexible array is employed in several embodiments and is selectively bent or flexed to vary its radius of curvature and thus control the focal point and/or a direction of focus of the array. In another embodiment, each of the transducer elements comprising the array are individually mechanically pivotable to steer the ultrasonic beam produced by the transducer elements.

22 Claims, 13 Drawing Sheets

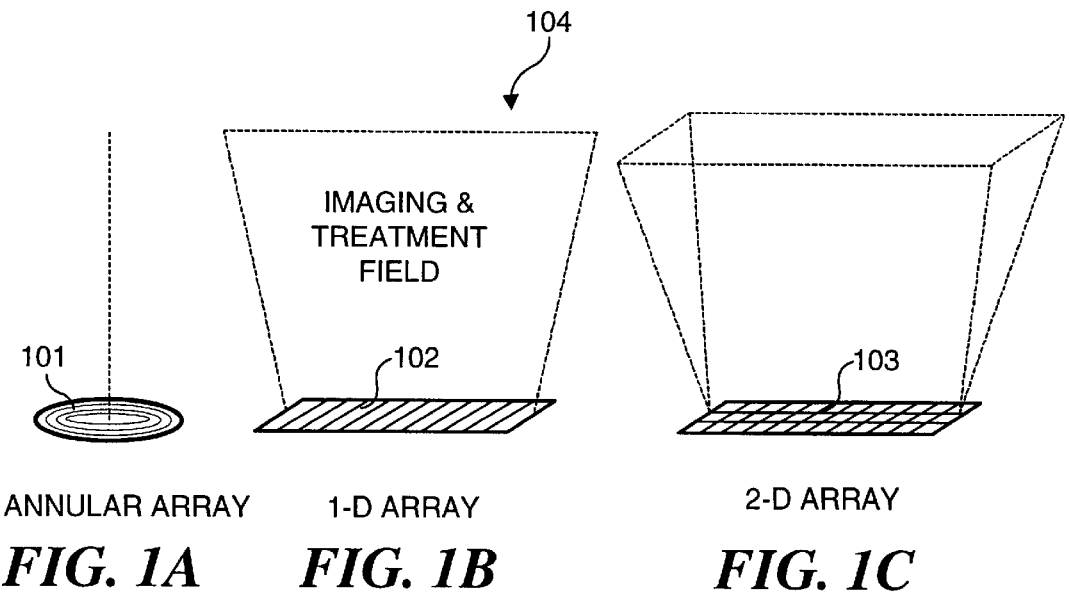
ANNULAR ARRAY
FIG. 1A
1-D ARRAY
FIG. 1B
2-D ARRAY
FIG. 1C
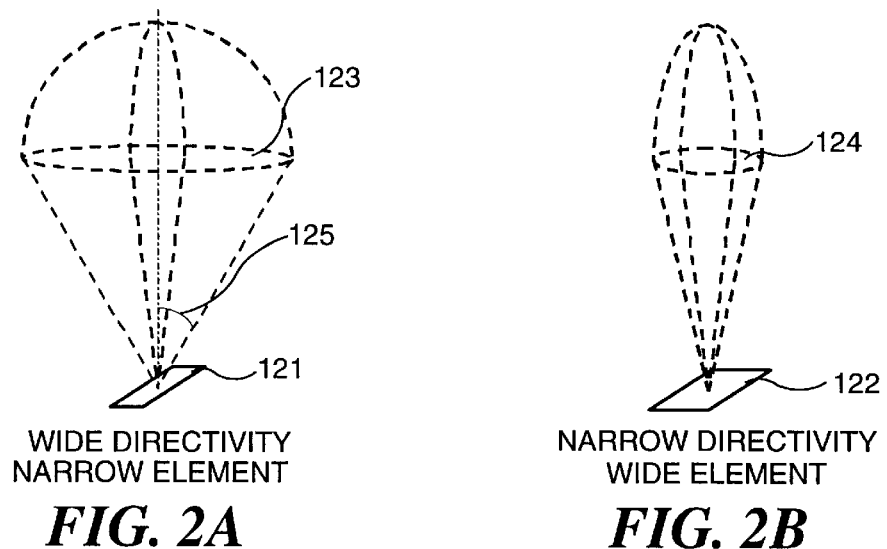
WIDE DIRECTIVITY
NARROW ELEMENT
FIG. 2A
NARROW DIRECTIVITY
WIDE ELEMENT
FIG. 2B

WITHOUT BEAM STEERING

WITH BEAM STEERING

WIDE IMAGING FOV

DEEP THERAPY

SHALLOW THERAPY

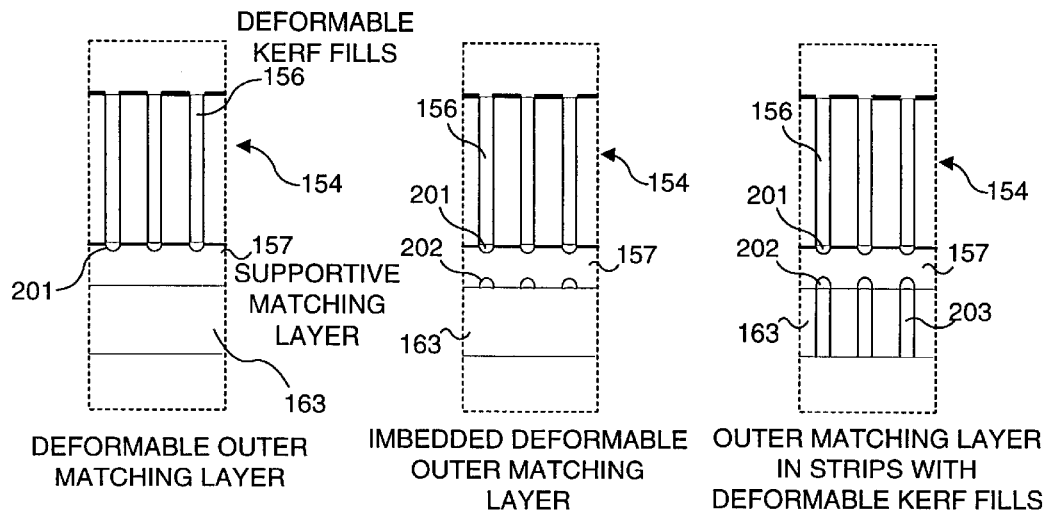
FIG. 11A  DEFORMABLE OUTER MATCHING LAYER
FIG. 11B  IMBEDDED DEFORMABLE OUTER MATCHING LAYER
FIG. 11C  OUTER MATCHING LAYER IN STRIPS WITH DEFORMABLE KERF FILLS
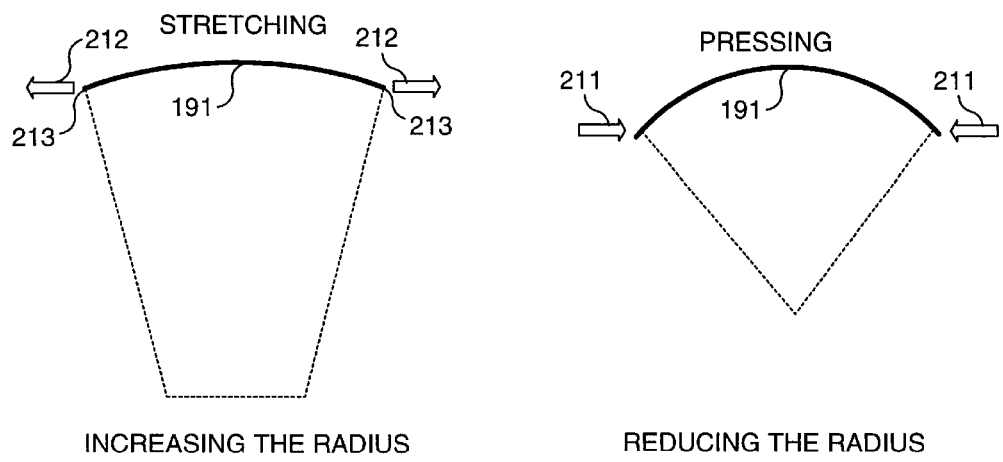
FIG. 12A  INCREASING THE RADIUS
FIG. 12B  REDUCING THE RADIUS

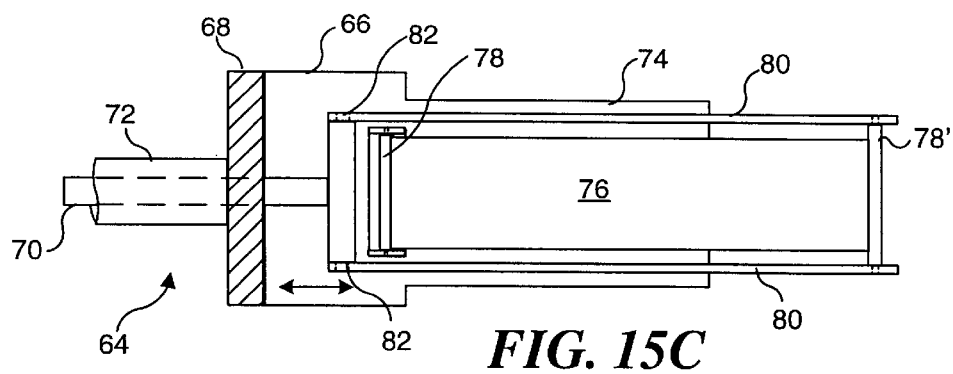
FIG. 15C
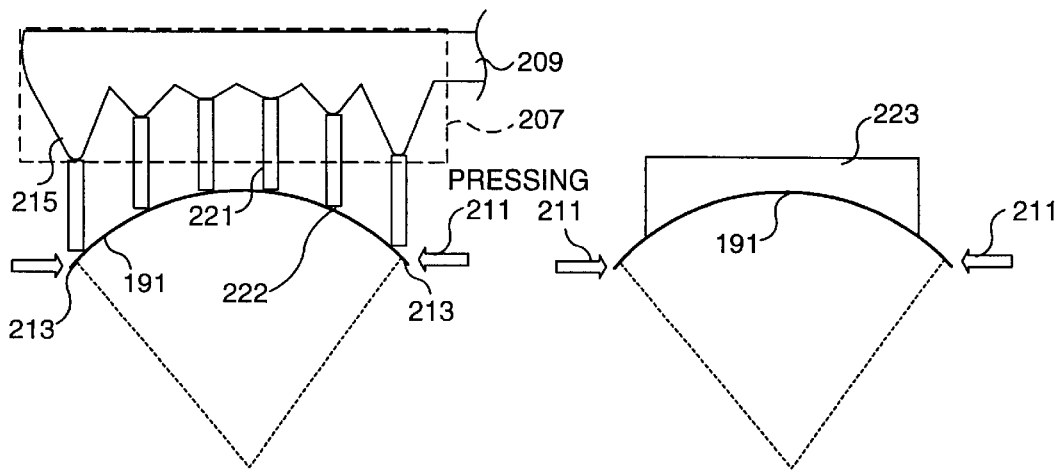
STOP PINS
FIG. 16A
STOP TEMPLATE
FIG. 16B
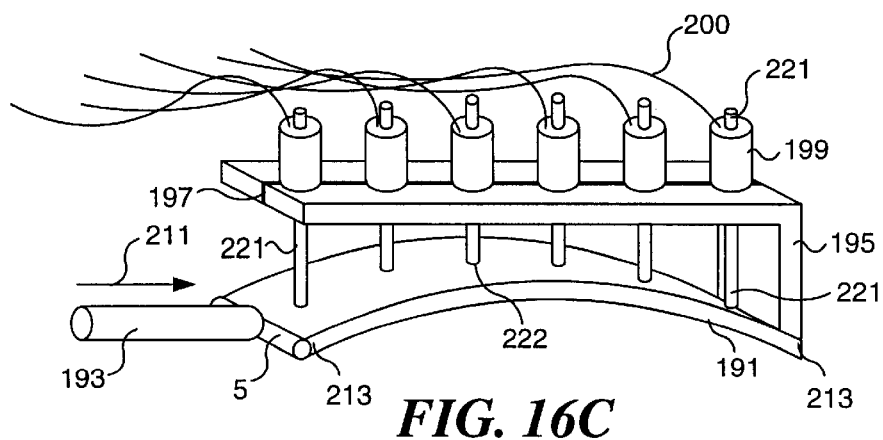
FIG. 16C

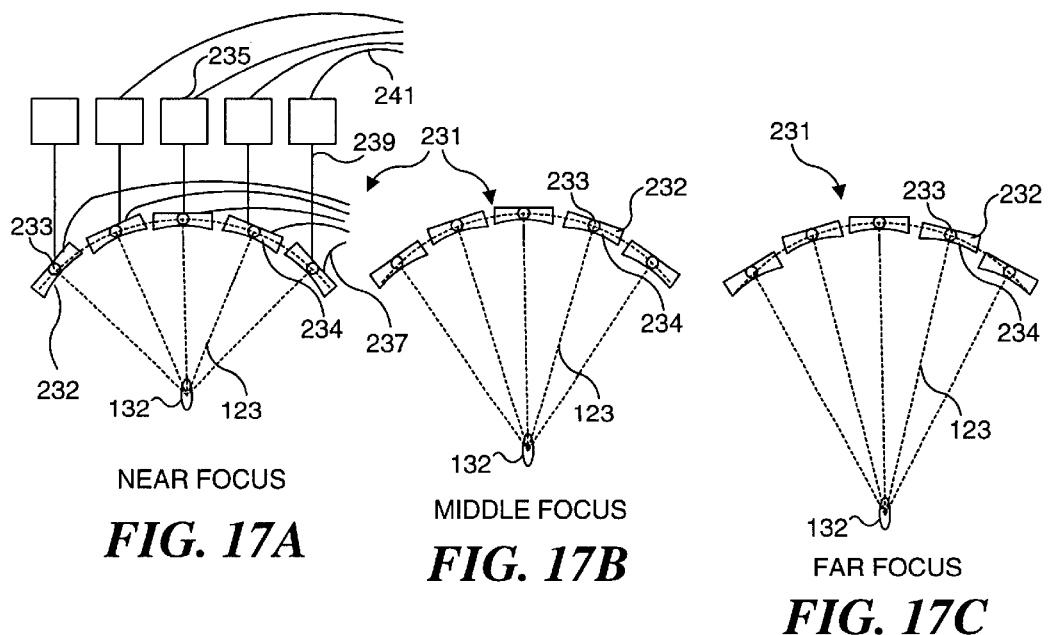
FIG. 17A NEAR FOCUS
FIG. 17B MIDDLE FOCUS
FIG. 17C FAR FOCUS
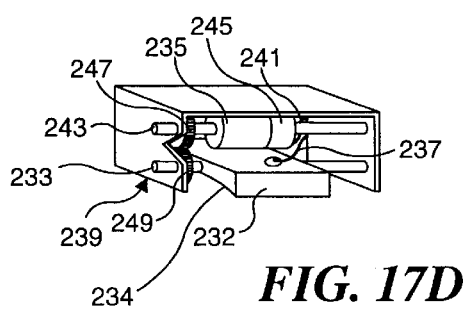
FIG. 17D
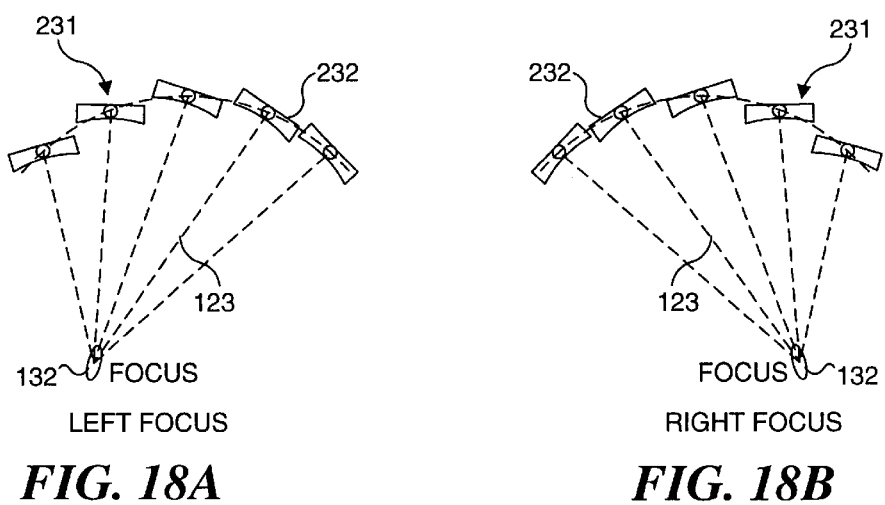
FIG. 18A LEFT FOCUS
FIG. 18B RIGHT FOCUS

ULTRASOUND TRANSDUCERS FOR IMAGING AND THERAPY

RELATED APPLICATIONS

This application is based on U.S. provisional patent application, Ser. No. 60/171,703, filed Dec. 23, 1999, the benefit of the filing date of which is hereby claimed under 35 U.S.C. §119(e).

FIELD OF THE INVENTION

The present invention generally relates to use of ultrasound for imaging and therapeutic purposes, and more specifically, to simplified ultrasound transducers that are both highly efficient for administering therapy and produce a wide bandwidth ultrasound signal for diagnostic imaging.

BACKGROUND OF THE INVENTION

Ultrasound is a term that refers to acoustic waves having a frequency above the upper limit of the human audible range (i.e., above 20 kHz). Because of their relatively short wavelength, ultrasound waves are able to penetrate into the human body. Based on this property, ultrasound in the frequency range of 2–20 MHz has been widely used to image internal human organs for diagnostic purposes.

To avoid thermal damage to tissue, the power level in diagnostic ultrasound imaging is kept very low. The typical ultrasound intensity (power per unit area) used in imaging is less than 0.1 watt per square centimeter. High intensity focused ultrasound, which can have an intensity above 1000 watts per square centimeter, can raise the tissue temperature at the region of the spatial focus to above 60 degrees Celsius in a few seconds and can cause tissue necrosis almost instantaneously.

High intensity ultrasound has been proposed to treat and destroy tissues in the liver (G. ter Haar, "Ultrasound Focal Beam Surgery," Ultrasound in Medicine and Biology, Vol. 21, No. 9, pp.1089–1100, 1995); in the prostate (N. T. Sanghvi and R. H. Hawes, "High-intensity Focused Ultrasound," Experimental and Investigational Endoscopy, Vol. 4, No. 2, pp.383–395, 1994); and in other organs.

Ultrasound transducers generate ultrasound waves for imaging and therapy. A typical ultrasound transducer comprises piezoelectric materials such as PZT ceramics, electrodes, matching layers, and backing materials. When an electrical field is applied to two electrodes on the opposite sides of a piezoelectric ceramic plate, the thickness of the plate expands or contracts, depending on the polarity of the field. If the electrical field polarity alternates at a high frequency above 20 kHz, the mechanical vibration caused by the rapid expansion/contraction of the plate generates ultrasound waves.

During ultrasound therapy, high electrical power is applied to the ultrasound transducer to generate a correspondingly high acoustical output power. Transducer power conversion efficiency is the ratio of the output acoustic power to the input electrical power. A high transducer power conversion efficiency is always desirable to minimize the transducer internal heating due to electrical power losses.

During ultrasound imaging, low-power electrical pulses drive the transducer, causing it to transmit the low power ultrasound pulses into the patient body. Ultrasound echoes, reflected from organ boundaries and other tissue and physiological structures within the body, are typically received by the same ultrasound transducer and converted to electrical output signals, which are processed to produce ultrasound images of the internal organ on a display. A transducer having a broad frequency bandwidth is desirable to obtain good image resolution. Often, however, the desire for high efficiency during ultrasound therapy and the desire for broad bandwidth during ultrasound imaging are difficult to satisfy simultaneously in the same transducer design.

To treat or to image a large volume of diseased tissue, the ultrasound beam is caused to scan through the tissue, either mechanically or electronically. In a mechanical scanning device, such as disclosed in U.S. Pat. No. 4,938,216, one or more electrical motors position the ultrasound transducer in different positions. One of the more common types of electronic scanning device employs an ultrasound linear phased-array transducer, such as that disclosed by E. B. Hutchinson and K. Hynynen, in an article entitled "Intracavitary Ultrasound Phased Arrays for Noninvasive Prostate Surgery" (IEEE Transactions on Ultrasonics, Ferroelectrics, and Frequency Control, vol. 43, No. 6, pp.1032–1042, (1996)), and in U.S. Pat. No. 4,938,217. An electronic scanning device has a plurality of small piezoelectric elements disposed in an array. These elements are independently driven. By properly controlling the phase of the driving signals applied to energize these elements, the array will be caused to form ultrasound beams directed at different depths and angles. The electronic scanning transducer has many advantages over the mechanically scanned transducer. The main advantage is that there are no moving components in the electronic device, so that it has much higher durability and reliability. The disadvantage of the electronic device is its complexity and associated relatively high cost. To achieve a compromise between the advantages and the disadvantages, some prior art references, such as U.S. Pat. No. 4,757,820, disclose transducer designs that include both the mechanical and the electronic approaches.

However, system and transducer complexity is still one of the major disadvantages of electronic therapeutic arrays. A therapeutic transducer requires a large surface area to generate a high acoustic power output and a large aperture for deep treatment. Preferably, the f-number (focal depth over aperture size) is kept constant within the range from 0.8 to 2.5. On the other hand, to steer the ultrasound beam over a wide range and to focus the beam using a small f-number, the ultrasound phased array must have very fine, narrow array elements, because a narrow element can transmit an ultrasound beam throughout a wide range of directions.

To provide a transducer having both a large aperture and fine elements to enable it to provide imaging and therapy functions, a conventional therapeutic phased array design includes a very large number of elements. For example, to treat lesions at a maximum depth of 5 cm, a therapeutic linear array having an f-number of 1.0 should have an aperture width of about 5 cm. For use at this depth, the transducer will typically operate at a frequency of about 3 MHz. The wavelength of ultrasound in water or biological soft tissue at this frequency is about 0.5 mm. For a phased array of this configuration to have a sharp focus (i.e., a relatively small f-number), the array typically will have an element pitch size about 0.5 to 0.7 times the wavelength of the ultrasound beam it produces. For a pitch size of about 0.6 times the wavelength, an exemplary therapeutic array might have an element pitch size of about 0.3 mm and a total of about 167 elements.

Each element has a dedicated electronic driving circuit in a control system for the array. To drive a phased array like that discussed above, the control system would need to include 167 sets of driving circuits, i.e., one for each element. The array and the control system are connected through a thick cable that includes at least 167 smaller coaxial cables inside it. Each smaller coaxial cable should have conductors of a sufficiently large cross-sectional area to carry a relatively large current to the therapeutic array element. The thick cable required to meet this need makes the device difficult to handle.

Considering all these constraints, it will be evident that the complexity of such a therapeutic phased array, including the cable and the control system coupled to it, can easily become impractical to engineer, and its cost will most certainly exceed the budget of most medical facilities. It is for these reasons that the therapeutic phased array has not been widely accepted.

It would be desirable to use an ultrasound array transducer for both imaging and therapy. The smaller size of a probe having a transducer that is usable for both functions is an advantage. For example, in many endoscopic, therapeutic-ultrasound applications, there are limitations on the size of the treatment devices that can be employed. Thus, a dual-purpose ultrasound array transducer may save space in the probe. Also, in ultrasound image-guided therapeutic applications, there are two spatial planes, one for imaging and the other for treatment. These two planes should overlap so that the treatment area can be observed in the imaging plane. Oftentimes, however, it is difficult to register the two planes from two spaced-apart transducers. Sometimes, there are blind spots in the treatment zone, which are not observable in the imaging plane. However, if one transducer is used both for imaging and treatment, the problem of non-overlapping zones does not arise.

The prior art has not dealt extensively with the problem of designing a dual-purpose phased array transducer. Besides the conflict between the disparate design parameters that must be satisfied to achieve efficiency and adequate bandwidth in such a transducer, as noted above, there are other unresolved issues in making a therapeutic phased array transducer, such as heat dissipation, and element cross-talk. In U.S. Pat. No. 6,050,943 and in an article published by P. G. Barthe and M. H. Slayton, entitled "Efficient Wideband Linear Arrays for Imaging and Therapy" (IEEE Symposium in Ultrasonics, Ferroelectrics and Frequency Control, November 1999), the authors address some of these problems.

Thus, there is a clear need for an ultrasound device that employs simple and highly efficient ultrasound transducer arrays usable for both imaging and therapy. This kind of ultrasound device can be used to generate real-time ultrasound images of a patient's internal condition, provide ultrasound therapy to a treatment site, and monitor the treatment results. Such an ultrasound transducer should have variable geometry for treating different pathologies. In addition, the transducer array should be capable of generating high-intensity ultrasound to ablate or necrose tumors and other diseased tissues.

SUMMARY OF THE INVENTION

The present invention provides an ultrasound transducer apparatus comprising a generally concave array of ultrasound transducer elements. The apparatus enables a reduced number of transducer elements and a larger pitch size compared to that used for the elements in a traditional linear array of transducer elements. Reducing the number of elements also reduces the required number of connection cables and control channels. While providing the same performance, the concave array system is much simpler and less costly than a conventional linear phased array system.

The concave geometry also requires smaller phase differences between transducer elements, thus reducing cross-talk and heating in kerf fills between elements. The geometry also reduces the affect of grating lobe problems during the beam-forming process.

To provide both imaging and therapy functions, one embodiment of the present invention includes circuitry to rapidly switch between low and high Q-factors. Alternatively, the invention may include one transducer array for imaging and another transducer array for therapy, enabling one of the arrays to selectively act on a target site. For example, the imaging transducer array and therapeutic transducer array may be attached to opposite sides of a rotatable carriage and alternately directed to the target site as the carriage rotates.

To control a location of a focus point of the transducer array, one form of the invention includes a beam steering mechanism, or controller, to adjust the phases or the delays of signals that drive the transducer elements. To increase the transducer bandwidth for better image resolution, an electrical damping circuit can be included to provide the equivalent of a mechanical backing. One or more material acoustic matching layers and/or air backing can optionally be included to improve the transducer efficiency and bandwidth. In addition, the present invention may optionally include one or more metal matching layers to improve heat dissipation by the transducer.

A flexible transducer array is preferably provided to control the location of the focus point. Flexible outer layers and kerf fills between transducer elements enable the array to bend in different curvatures. As with a fixed curvature array, the flexible array reduces the number of required transducer elements. However, the flexible array embodiment also enables a practitioner to adjust the imaging field of view (FOV) and simplifies control of the treatment focusing, by changing the geometric shape of the array.

To facilitate these capabilities, the invention may include a geometry control mechanism. Preferably, the control mechanism and flexible transducer array comprise a laparoscopic applicator in which a linear actuator translates one end of the flexible transducer array relative to an opposite fixed end, causing the transducer array to flex into a desired curved shape. The actuator alternatively comprises either a manual adjustable shaft or a motor-driven threaded shaft, shuttle block, push rod, or the like. Another embodiment includes position stops or a position template to guide the curvature of the array, so that the array matches the profile of the position stops or template. The position stops or template may be preset, or adjustable. The geometry control mechanism may also be independently applied to one transducer array that is dedicated to one of the functions of imaging or therapy, while another transducer array is dedicated to the other function. For example, in a laparoscopic applicator, the control mechanism may be applied to a therapy transducer array connected to a rotational carriage, while an imaging transducer array is attached to the opposite side of the rotational carriage and is not provided with any control mechanism.

Another embodiment of the invention includes a plurality of transducer arrays, each directed toward a common focus point. Using multiple transducer arrays enables each array to contain fewer transducer elements and provides a relatively wide imaging and treatment field. Each transducer array may also be allowed to pivot about a pivot point, such that controlled pivoting of the multiple transducer arrays controls the location of the common focus point. This enables controlled movement of the common focus point in at least two directions.

Another aspect of the invention includes a transducer manufacturing method to produce an ultrasound transducer apparatus with a generally concave geometry. The method comprises the step of providing kerf fills having a non-uniform stiffness to control the curvature of the transducer array. For example, providing kerf fills with a symmetrically non-uniform stiffness improves the likelihood of obtaining a symmetric semi-circle shape of the array, rather than a parabolic shape, when moving one end of a transducer array, compared to an array that has uniformly stiff kerf fills. Alternatively, or in addition, the method may include the step of providing support layers having a non-uniform stiffness. Another step of the method preferably includes cutting grooves into a metal support layer between the transducer elements on the side of the support layer that supports the transducer elements to avoid bonding between the transducer element and the metal support layer. Further steps optionally include cutting grooves into an opposite side of the support layer, and casting an outer matching layer over the support layer and into the grooves to improve the bonding strength between the support layer and an outer matching layer. If the outer matching layers, or support layers, are not deformable, alternate steps to provide flexibility include cutting the outer matching layer into thin strips after bonding the outer matching layer to the support layer, and then filling the kerfs with deformable material.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein:

FIGS. 1A–1C illustrate different ultrasound arrays and their imaging/treatment fields according to the invention;

FIGS. 2A and 2B illustrate different beam directivities of narrow and wide transducer elements;

FIGS. 11A–11C are diagrams of different structures of the proposed flexible array;

FIGS. 12A and 12B are diagrams illustrating changing the radius of the flexible array according to the invention;

Figure 19:
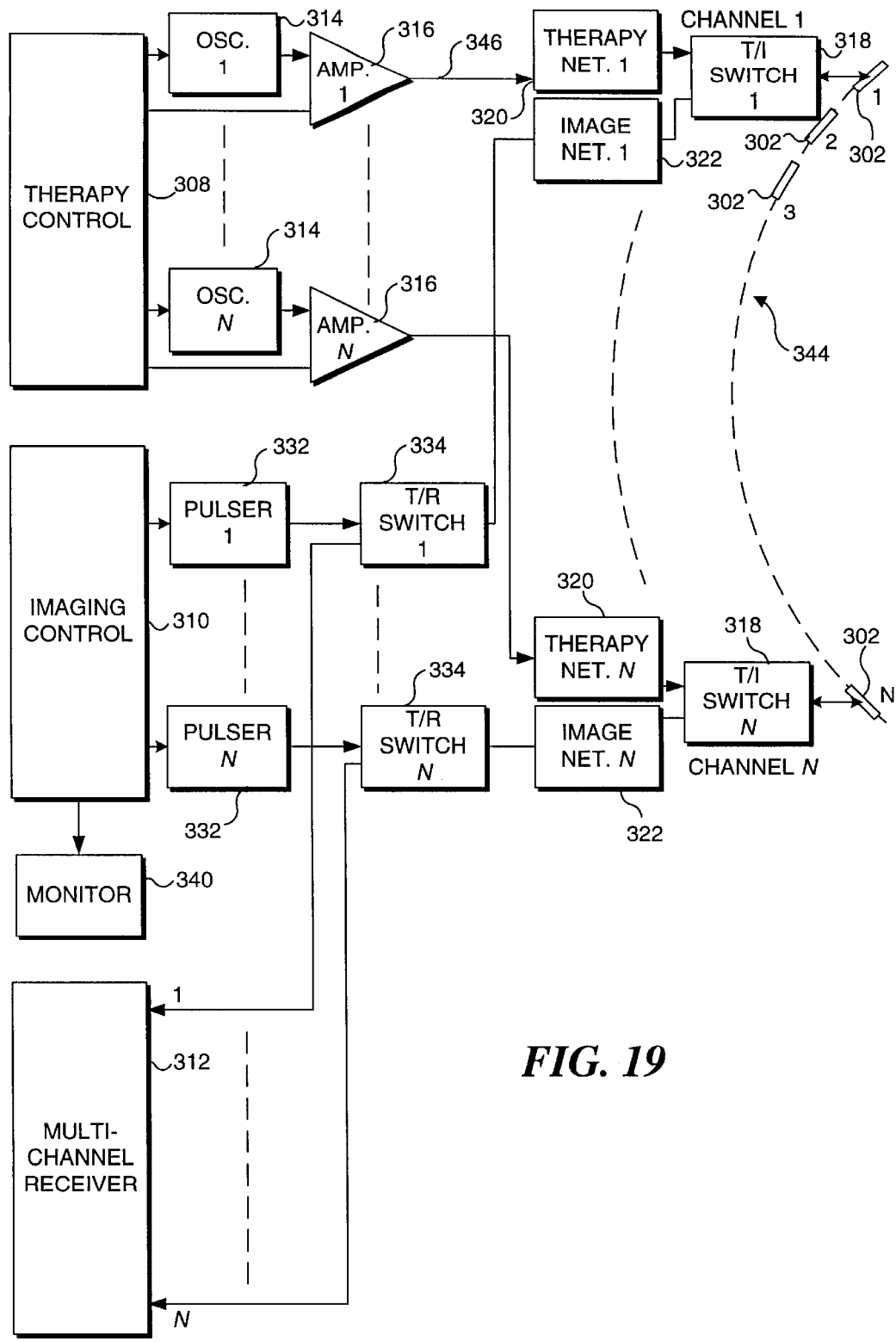

FIGS. 13A–13D, 14A–14C, and 15A–15C are diagrams of several applicator assemblies using the flexible array concept according to the present invention;

FIGS. 16A–16C are schematic diagrams illustrating three embodiments for controlling the shape of the flexible array;

FIGS. 17A–17C illustrate beam focusing using the mechanical array according to the invention;

FIG. 17D is a schematic diagram showing a micro-motor and encoder assembly for mechanically rotating transducer array elements like those in FIGS. 17A–17C;

FIGS. 18A and 18B illustrate beam steering using the mechanical array according to the invention; and FIG. 19 illustrates a control system suitable for use with any of the embodiments of the applicators that include the present invention.

DESCRIPTION OF THE PREFERRED EMBODIMENT

An ultrasound array includes many small transducer elements on its aperture surface, and these transducer elements can be distributed in several different geometric arrangements, as shown in FIGS. 1A–1C. Each transducer element is independently driven by its own electronic circuitry. An annular array (FIG. 1A) includes many coaxial ring elements 101. A one-dimensional (1-D) array (FIG. 1B) includes many elongate row elements 102 arranged side-by-side and extending transversely across the longitudinal axis of the array. A 1½-D or two-dimensional (2-D) array (FIG. 1C) includes a matrix of elements 103 distributed over two dimensions. The 1-D array has the advantage of simplicity and is therefore a preferred configuration for use in the present invention. The same advantages of the invention described herein can also be achieved using 1½-D and 2-D arrays. The 1-D array has a 2-D imaging and treatment field 104, or plane that extends along the longitudinal axis of the array.

Driven electrically near its resonant frequency, an ultrasonic transducer element generates an acoustic field. The coverage of the acoustic field within −6 dB of it maximum intensity is called the directivity of the element. As shown in FIGS. 2A and 2B, for a given frequency, a narrower element 121 has a wider directivity than a relatively wider element 122. The width of the ultrasonic transducer element directivity is referred to as its acceptance angle in ultrasound imaging. In FIG. 2A, an acceptance angle 125 is indicated. When the element width is reduced to near one half of the ultrasound wavelength in the propagating media (water or tissue in this case), the acceptance angle ranges from −90° to +90°. The element directivity determines the array's ability to focus and steer its ultrasound beam. A wider directivity provides an array with a sharper focus and wider steering capability. For this reason, narrow transducer elements are always desirable. On the other hand, a larger number of narrower elements are required in an array to provide a given aperture size.

Concave Array

Figure 3:
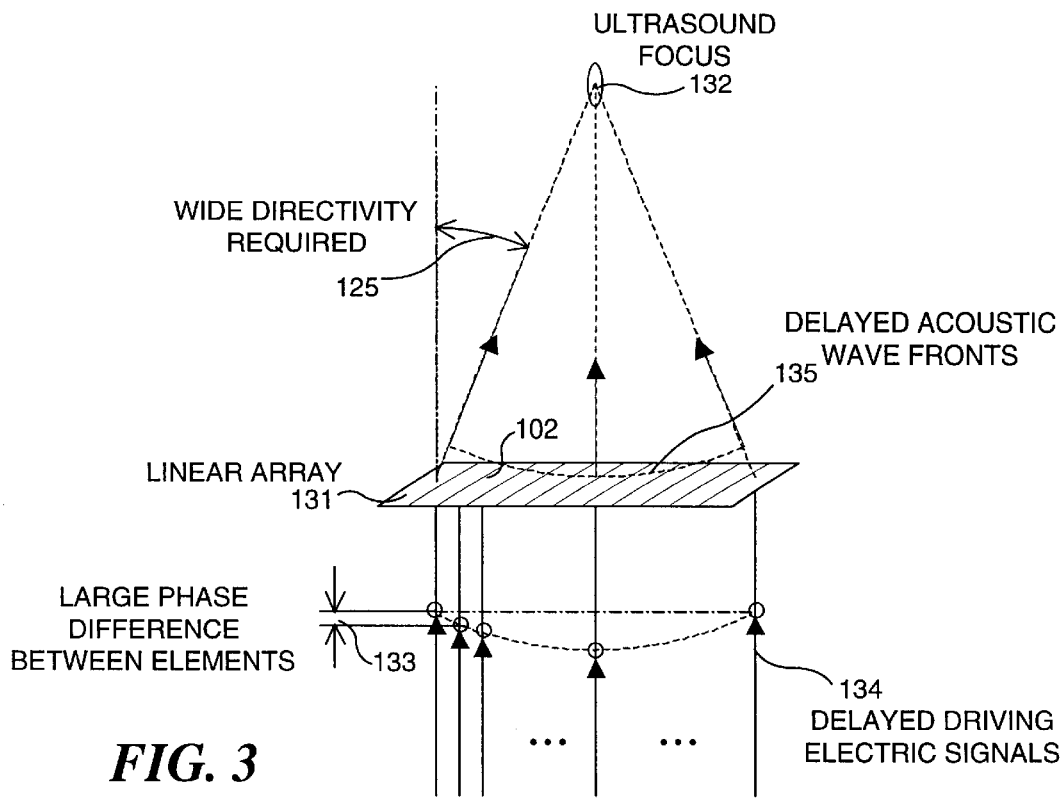
FIG. 3 illustrates the mechanism of electronic beam focusing of an ultrasound linear phased array.
Figure 4:
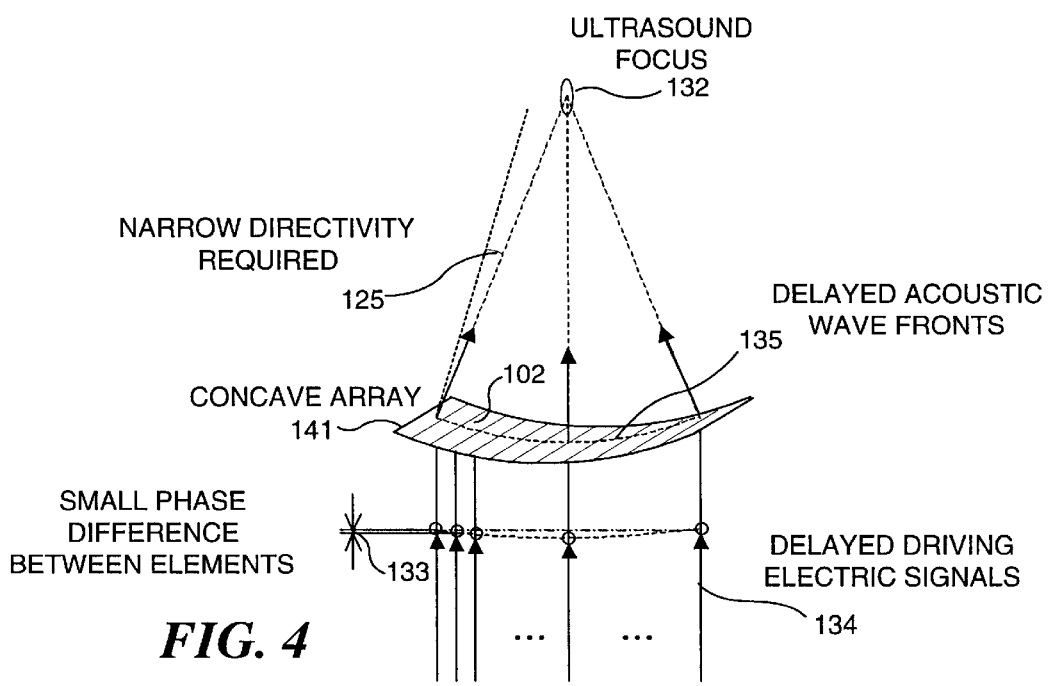
FIG. 4 illustrates the mechanism of electronic beam focusing of a concave ultrasound array.

For many applications of high-intensity ultrasound therapy, the ultrasound power from the array elements must be sharply focused. This goal is typically accomplished by electronic focusing of the array. As illustrated in FIGS. 3 and 4, electronic focusing changes the arrival time, or the phase relationship of the electrical driving signals 134 supplied to different transducer elements 102, so that acoustic wave fronts 135 generated by the transducer elements arrive at a desired ultrasound focus 132 at the same time, or in phase. These waves add coherently to give the highest ultrasound intensity at the focus. The concept of electronic focusing, as used in the present invention, is illustrated in FIG. 3, for a typical linear phased array 131, and in FIG. 4, for a concave array 141. It should be apparent that to achieve a given ultrasound focus 132 with a small f-number (i.e., 0.8 to 2.5), concave array 141 requires much less signal delay or phase difference 133 and has a much smaller acceptance angle 125 than linear array 131. The smaller acceptance angle of the concave array makes it possible to use a larger element size, or to use fewer elements, so that the cost and the complexity of the concave array and the control system that drives it are reduced, compared to the linear array. The smaller phase difference 133 between adjacent elements of the concave array also reduces the problems of grating lobes, element cross-talk, and heating in kerf fills of the array.

Figure 5:
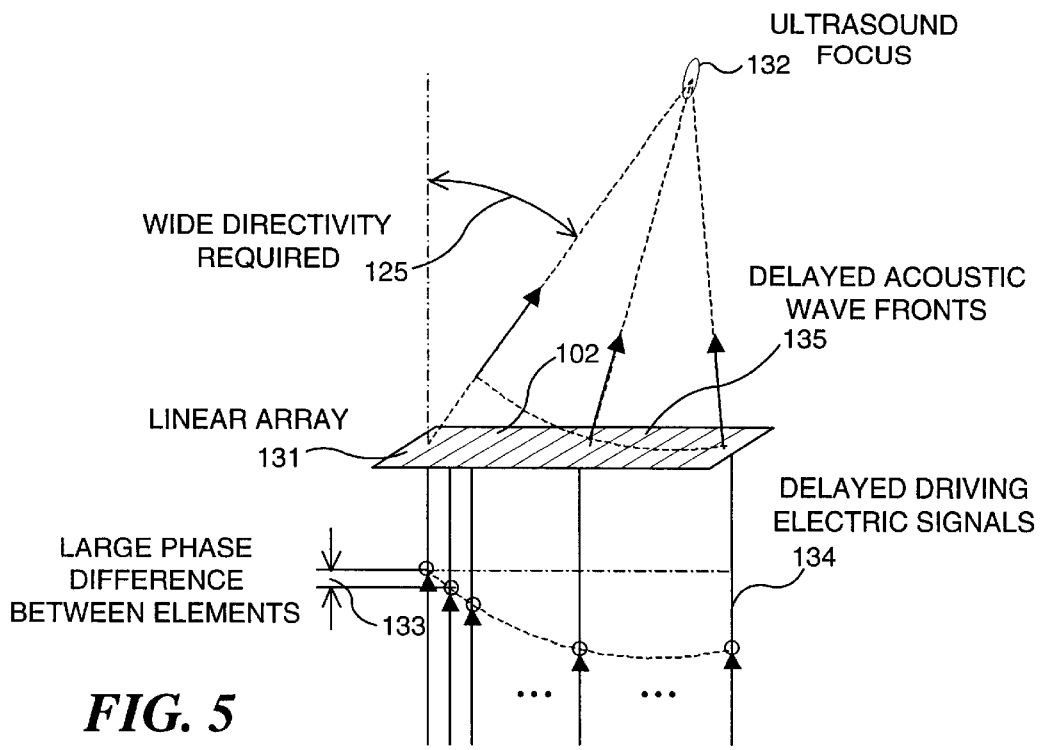
FIG. 5 illustrates the mechanism of electronic beam steering of an ultrasound linear phased array.
Figure 6:
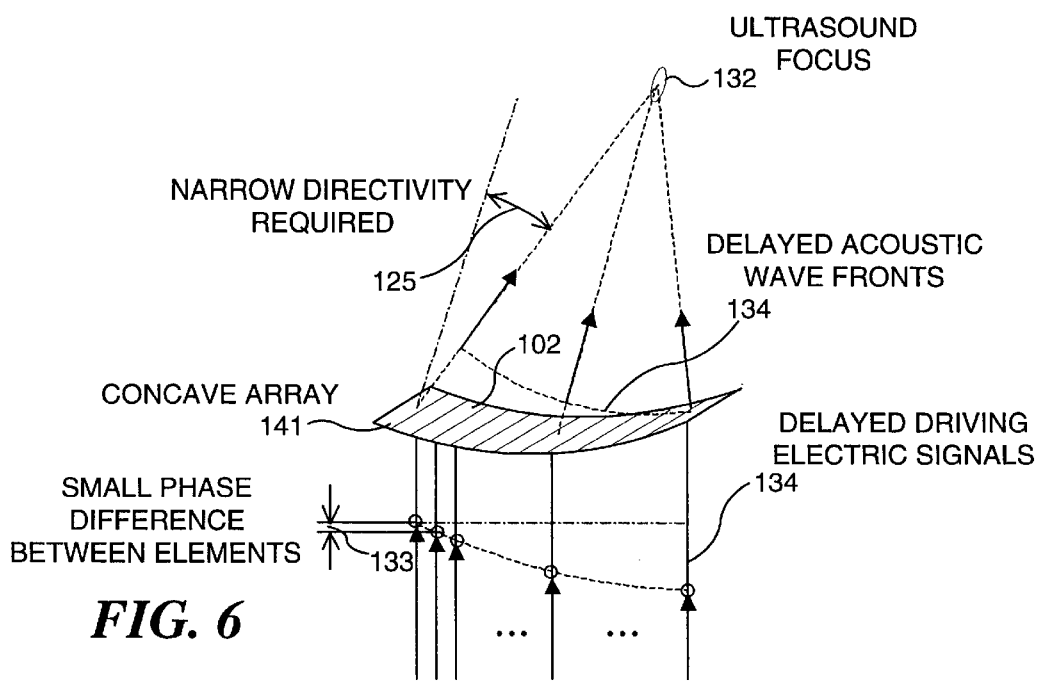
FIG. 6 illustrates the mechanism of electronic beam steering of a concave ultrasound array.

To treat a large area of tissue, an ultrasound device should be able to scan its focal point over the area. In a manner similar to electronic beam focusing, array beam steering is achieved by adjusting the phases or the delays of driving signals 134 that are applied to the ultrasound transducer elements. This steering mechanism is shown in FIGS. 5 and 6 for linear array 131 and for concave array 141, respectively. In electronic beam steering, as in electronic focusing, concave array 141 has a much smaller acceptance angle 125 and requires much less phase difference 133 between elements than linear array 131, within a therapeutic range (i.e., for an f-number in the range 1.0–1.5).

Figure 7A:
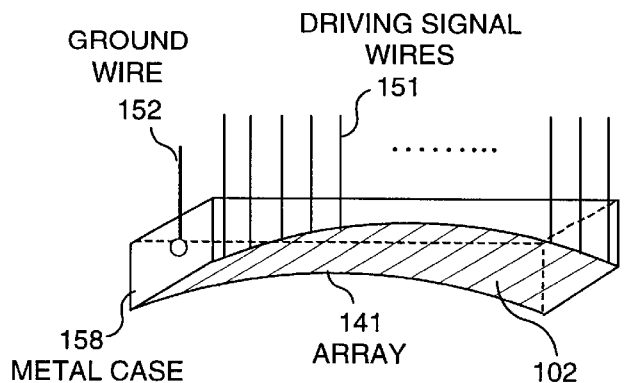
FIG. 7A is a simplified diagram of the overall structure of the concave array according to the invention.
Figure 7B:
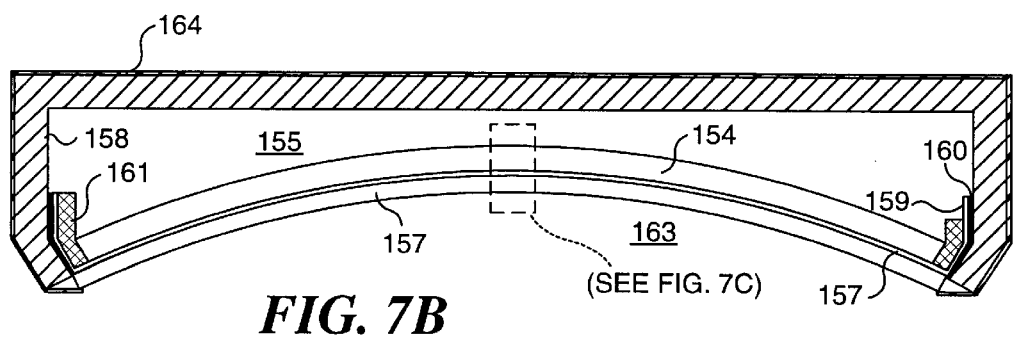
FIG. 7B is a cross-sectional view of the structure of the concave array according to the invention.
Figure 7C:
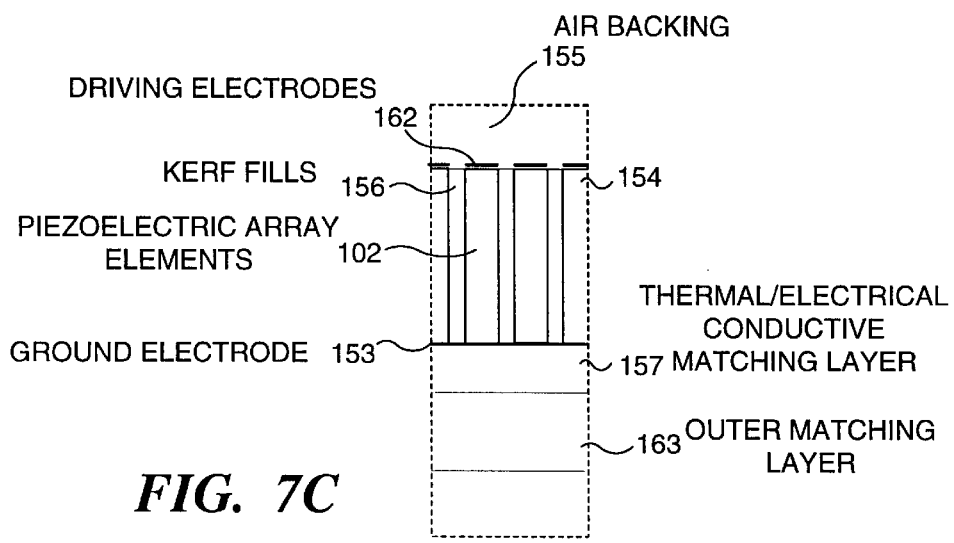
FIG. 7C is a zoom view of the array cross-sectional detail.

With reference to FIGS. 7A, 7B, and 7C, concave array 141 comprises a plurality of array elements 102 that are connected through driving signal wires 151 to a control system (not shown). A common ground wire 152 is connected to a common ground electrode 153 of the elements and to a metal case 158 that provides support and backing for the elements. Details of a small section of the concave array are illustrated in FIG. 7C. The concave array includes a piezoelectric array element layer 154, which is the innermost layer (i.e., disposed more inside the metal case, and is preferably provided with an air backing 155 for high efficiency. Array elements 102 are diced or cut from a piezoelectric plate, which is fabricated, for example, of PZT ceramic. Most importantly, array elements 102 may be diced from a 2-2 or 1-3 composite material comprising PZT ceramic and high temperature epoxy mixed with thermally conductive particles, such as boron nitride. Such a piezoceramic composite will reduce undesired lateral, vibration modes that would otherwise result due to the array element size. It must also be emphasized that this piezo-ceramic composite material can be used in fabricating an ultrasound transducer that includes a single flexible ultrasound emitting element that can be curved in a desired shape to control a focus of the ultrasound beam that it emits and/or to steer the ultrasound beam in a desired direction. Examples of this single element transducer are discussed below in regard to the embodiments of FIGS. 13A–13D, 14A–14C, 15A–15C, and 16A–16C.

There are electrodes on the both sides of the piezoelectric plate, so that each transducer array element 102 includes its own driving electrode 162 and ground electrode 153. Kerfs between the array elements are filled with a non-piezoelectric material 156, such as epoxy mixed with absorptive particles, or alternatively are left unfilled. A middle layer 157 comprises a thermally and electrically conductive material, such as aluminum, titanium, or graphite.

Middle layer 157 provides four functions for the transducer. First, it connects ground electrodes 153 of all of the array elements together and couples with the ground potential of the metal housing. Second, the middle layer conducts heat generated within the array outside it so that the heat is better dissipated. The rim of the middle layer is bonded to metal case 158, which serves as a heat sink. Third, middle layer 157 is the inner acoustic matching layer of the array and should therefore preferably have an acoustic impedance lower than that of the piezoelectric ceramic. To maximize the transducer efficiency, the thickness of the middle layer is properly controlled to provide appropriate impedance matching between the ceramic and the tissue to which the ultrasound is being coupled. Finally, the middle layer provides mechanical strength to the overall array structure, especially when there are the kerfs are not filled. Aluminum is a preferred material for the middle layer because of its low acoustic impedance, good thermal conductivity, good mechanical strength, and flexibility. A wrapped-over edge 159 of middle layer 157 is bonded to metal case 158 with a thermally and electrically conductive adhesive 160. A thin electrical insulator 161 is disposed between wrapped-over edge 159 and the array elements to prevent electrical breakdowns between driving electrodes 162 and ground. To further optimize the efficiency and broaden the transducer bandwidth, one or two outer matching layers 163 may optionally be included. Outer matching layer 163 has an impedance between that of inner matching layer 157 and the tissue. The thickness of one outer matching layer 163 is typically about one quarter wavelength of the transducer frequency and the outer matching layer comprises an electrically non-conductive material to insulate and prevent electrical leakage from middle layer 157, which is adjacent to ground electrodes 153. To completely seal the device, an electrically insulating coating 164 is applied over the outside surface of metal case 158.

For ultrasound imaging, use of a transducer having a wide frequency bandwidth provides a high resolution image. The quality factor, Q, of a transducer is the ratio its central frequency to its bandwidth. To ensure a wide bandwidth, the Q of an imaging transducer is typically made very low by using heavy backing materials and is electronically matched to the driving electronics in a control system by proper tuning. The Q is also the ratio of the transducer input electrical power to its output acoustic power. When administering high-intensity ultrasound therapy, the Q of the transducer should be very high to achieve a high efficiency. It is difficult to meet both requirements when a single ultrasound transducer is used for both imaging and therapy.

Figure 8A:
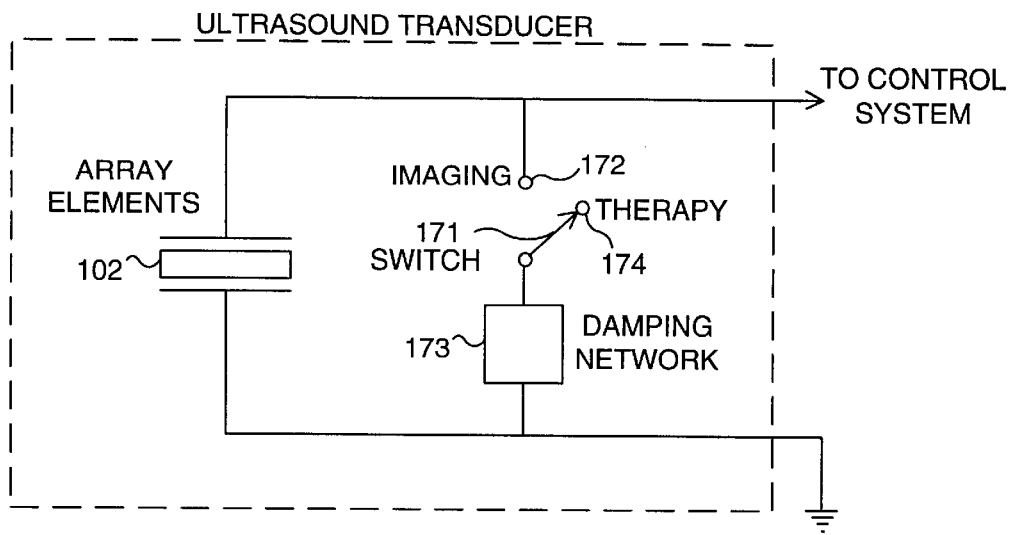
FIG. 8A is a diagram of a switch circuit for controlling the transducer Q-value for both imaging and therapy.
Figure 8B:
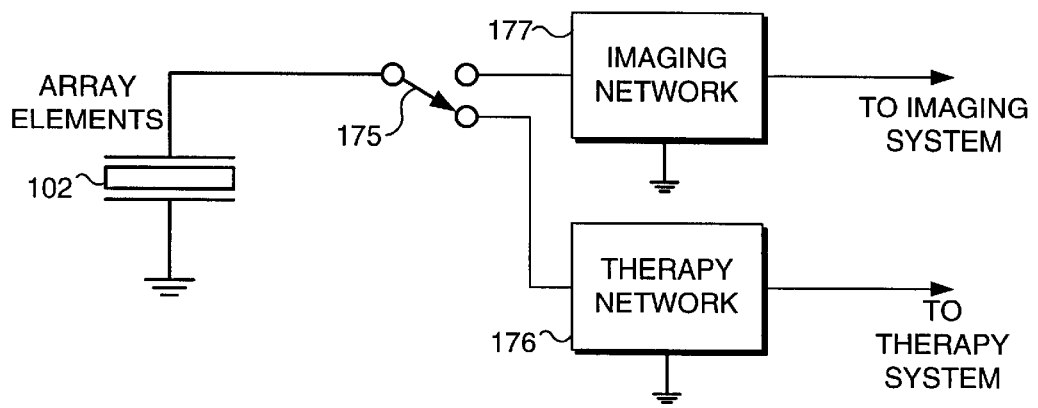
FIG. 8B is a diagram of a switch circuit that selects either an imaging damping network or a therapy damping network, depending upon an operational mode of the transducer.

To solve this problem, the present invention preferably includes an electronic switch 171 that is closed to reduce the transducer Q during imaging, as shown in FIG. 8. The transducer array is designed to have a relatively high Q when the switch is open. Accordingly, during therapy, electronic switch 171 is placed in an open position 174 so that the transducer exhibits a high Q and a high power efficiency. During imaging, the switch is moved to a closed position 172, which connects a damping network 173 in parallel with array elements 102. The lower-resistance provided by damping network 173 reduces the overall Q of the transducer, so that the bandwidth of the transducer becomes wider. FIG. 8A is intended to be a schematic representation of the concept. It will be understood that one electronic switch and one resistor may be connected to a single array element or to a group of the array elements. The parallel resistance can be provided by a single resistor or by a complex matching network including a plurality of resistive components. Because electronic switch 171 can be turned on or off very fast, the Q-factor of the transducer can be changed rapidly without changing its mechanical structure. As a result, real-time imaging and therapy can be interleaved rapidly. The same transducer selectively provides imaging and therapy, so that the efficacy and status of the ultrasound treatment process can be monitored in near real-time. It may also be advantageous to provide a selection between two matching networks, one providing damping characteristics appropriate for therapy and the other providing damping characteristics appropriate for imaging, as shown in FIG. 8B. An imaging network 177, when selected by a switch 175, provides an impedance matched, highly damped transducer configuration, while a therapy network 176, when selected by this switch, provides an impedance matched, weakly damped transducer configuration.

Cross-talk among array elements 102 is a serious problem in ultrasound imaging and therapy system design. When one array element is vibrating at its ultrasound frequency, a small amount of the vibration can propagate laterally to the adjacent elements. This linkage is called acoustic cross-talk. If the driving signal of adjacent elements is in phase and equal in amplitude to that of the leaking array element, the cross-talk may not cause any problem. When the adjacent elements are turned off, the cross-talk may slightly increase the equivalent aperture of the energized array elements in a manner similar to array apodization. (Note that apodization is a technique in which lower intensity driving signals are applied to array elements near the edge of an array to reduce the edge effect of an aperture.) The consequences may not be very significant, and may sometimes even be beneficial (for example, reducing the side lobes of the ultrasound beam). Cross-talk becomes problematic, however, when adjacent elements are not in phase during electronic focusing and steering, since the result may be an undesired change in the phase delays and distortion in the ultrasound beam. When transducer array elements are energized with a high driving power, the phase difference can create a substantial shear friction between adjacent elements. This friction is one source of thermal energy loss that causes overheating in the array, which may eventually damage the array. Concave array 141 requires a much smaller phase difference 133 during focusing and steering, as discussed above in regard to FIGS. 4 and 6, and consequently, the cross-talk between elements may have less adverse impact on its operation.

Figure 9A:
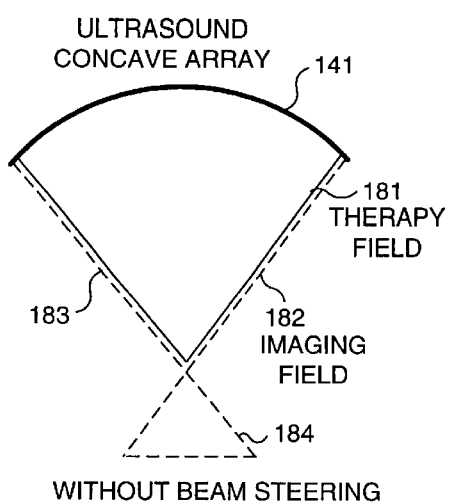
FIGS. 9A and 9B illustrate an imaging and therapy field without and with beam steering, respectively.
Figure 9B:
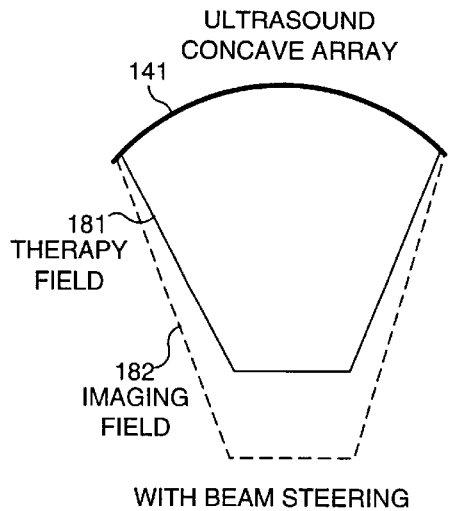

Without electronic focusing and steering, the geometric focus of concave array 141 is disposed near its spherical center. This feature further simplifies the designs of the transducer and the control system for some applications wherein a therapy field 181 has a sector shape as shown in FIG. 9A. During administration of the ultrasound therapy with the concave array, some or all array elements are connected together and driven by power supplied through only one coaxial cable from the control system (neither shown in FIG. 9A). Using the high-intensity ultrasound produced by concave array 141, the entire sector field can be necrosed without moving or steering the beam. Phase delays among array elements 102 are not required in this case. During imaging with concave array 141, a small group of array elements 102 are combined to form a small aperture. One ultrasound beam is transmitted by the small group of array elements, and returning echoes are received by the same small group of array elements comprising the aperture. Curvature of the concave array provides appropriate focusing, for both transmitting and receiving ultrasound, so that phase delays between array elements are unnecessary. The concave array's natural focusing greatly simplifies the ultrasound imaging system. Although electronic focusing might improve the image quality, the simple imaging capability of the concave array provides acceptable ultrasound images for treatment guidance. Without using electronic steering, the simple ultrasound imaging of concave array 141 has a FOV imaging field 182 shaped like a keyhole, as illustrated in FIG. 9A. A large sector portion 183 of the FOV matches the size and the shape of therapy field 181. A small triangle portion 184 beyond the apex of therapy field provides an extra FOV to monitor the tissue outside the treatment focus. This narrow FOV is a limitation of the simplified imaging system. If electronic focusing and steering are employed when energizing concave array 141, both imaging field 182 and therapy field 181 can selectively be made wider, as shown in FIG. 9B.

A Flexible Array

Figure 10A:
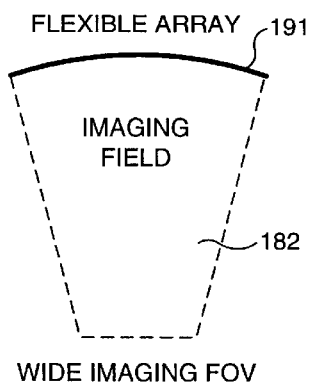
FIGS. 10A–10C are diagrams of a flexible ultrasound array for imaging and therapy.
Figure 10B:
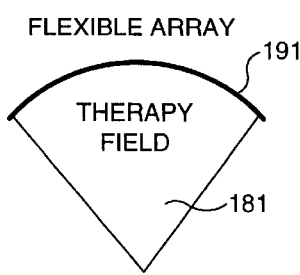
Figure 10C:
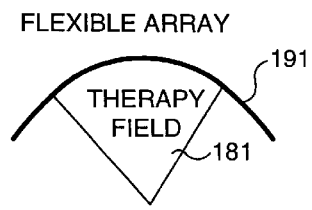

A flexible or deformable ultrasound concave array may provide both a wider FOV and yet, still require a simple imaging and therapy control system. In FIGS. 10A–10C, a flexible array 191 is illustrated and shown bent or flexed to different radii of curvature. By varying its curvature and without using electronic focusing and steering, flexible array 191 can thus produce different shapes of imaging and therapy fields, and its geometric focus can be adjusted to different depths. For ultrasound imaging, the flexible array is opened to be flatter, thereby producing a wide imaging FOV as shown in FIG. 10A. During ultrasound treatment, the array can be bent or flexed to obtain a small f-number and to achieve a desired treatment depth. To treat deep lesions during administration of ultrasound therapy, the whole flexible array is activated when flexed to achieve a relatively large radius of curvature corresponding to the maximum treatment depth, as shown in FIG. 10B. To treat shallow lesions, only part of the array is activated as shown in FIG. 10C, and the flexible array is bent or flexed to have a relatively small radius of curvature that focuses on the shallow depth.

Flexible array 191 has several significant advantages. For example, fewer array elements 102 are required for both imaging and therapy because electronic focusing and steering are not employed. Because the number of elements is less and no phase or time delay is required, the control system is much simpler. If electronic switches 171 (or a multiplexer—not shown) are included in the ultrasound applicator, close to the array, the number of wires 151 in the cable that extends between the applicator and the control system will be significantly reduced. Relays could alternatively be used instead of the switches in applications where the power per array element is relatively high and where the mode change time permits the use of relatively slower electromechanical switching devices such as relays. Furthermore, wide imaging FOV 182 can be employed to readily locate a lesion before ultrasound therapy of the lesion is initiated (during the treatment, a narrowed FOV can still provide real-time monitoring of the treatment area).

There are several ways to make ultrasound transducer arrays flexible. Essentially, in a multi-layer array structure like that shown in FIGS. 7B and 7C, one of the layers serves as a supportive membrane for the array elements as the array is flexed or bent. Use of a thin layer 157, which is preferably fabricated of aluminum or titanium and is disposed in the middle of the multi-layer structure is an ideal supportive layer for a flexible array. Layer 157 is preferably elastic and can be bent many times without being mechanically damaged. Other layers, if deformable, such as outer matching layers 163, are bonded to supportive layer 157 and are readily deformed during bending. Although piezoelectric ceramic layer 154 is not deformable, it comprises relatively thin strips of lead zirconate titanate (PZT) ceramic material that have been bonded to the supportive matching layer. Kerfs 156 between these strips are filled with soft deformable material that connects the thin strips together and allow the kerfs to expand and contract during bending.

To avoid the bonding between the ceramic strips and the metal supportive layer from being damaged during bending, a plurality of shallow grooves 201 are cut into supportive matching layer 157, as shown in FIG. 11A, so that each groove 201 is aligned with a different kerf 156. To improve the bonding strength between the supportive matching layer and deformable outer matching layer 163, a corresponding plurality of shallow grooves 202 are cut on the outer surface of the supportive matching layer 157, and the deformable outer matching layer 163 is cast over this outer surface, so that the inner surface of the outer matching layer is imbedded in grooves 202 (FIG. 11B). If the outer matching layer (or layers) 163 is not deformable, is also can be cut into thin strips and kerfs 203 between each such strip filled with deformable materials, as shown in FIG. 11C.

During ultrasound imaging and therapy, the flexible array is bent to a predetermined radius of curvature under the control of the user. There are many different mechanisms that can be used in the present invention to change the radius of the flexible array. Typically, any mechanism preferably employed for this purpose will apply a force that bends or flattens flexible array 191 by stretching or compressing ends 213 of the flexible array. FIGS. 12A and 12B include arrows 212 and 211 to indicate how a force is applied to ends 213 of the flexible array to stretch the ends apart and press the ends toward each other, thereby respectively increasing and decreasing the radius of curvature of the flexible array.

Figure 13A:
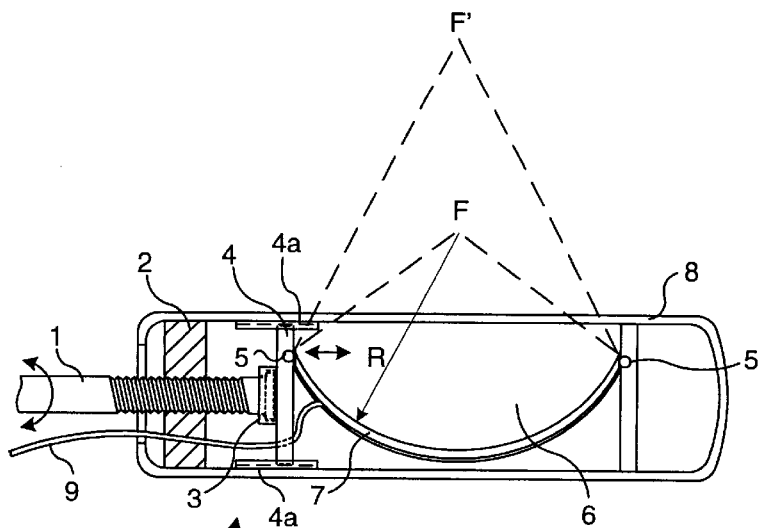

A number of useful ultrasound applicator embodiments employing the flexible transducer concept can be constructed in accord with the present invention. Again it must emphasized that a flexible transducer can comprise a single transducer element that is made of the piezo-ceramic composite material that is flexible and can be bent into a desired curved shape without breakage or other damage, or alternatively, can comprise a plurality of transducer elements in an array. FIG. 13A shows such an exemplary ultrasound applicator 50 that may be made using an elongate tubular housing 8 that is sufficiently small for laparoscopic applications (i.e., with a diameter of about 1 cm or less). In applicator 50, a threaded shaft 1 extends through a fixed turning block 2 and includes a rotatable end 3 captively and rotatably coupled to a sliding block 4. When threaded shaft 1 is rotated, it is threaded further into or out from fixed turning block 2 and causes sliding block 4 to slide within longitudinally extending grooved slides 4a. Rods 5 support the ends of a flexible transducer assembly 7 within a chamber 6, and one of these rods is connected to sliding block 4, while the other rod is fixed. A lead 9 conveys signals to and from flexible transducer assembly 7. As indicated above, flexible transducer assembly 7 can be a single transducer element that is flexible or a plurality of transducer elements configured in an array that is flexible and can be bent into a desired concave curved shape.

Figure 13B:
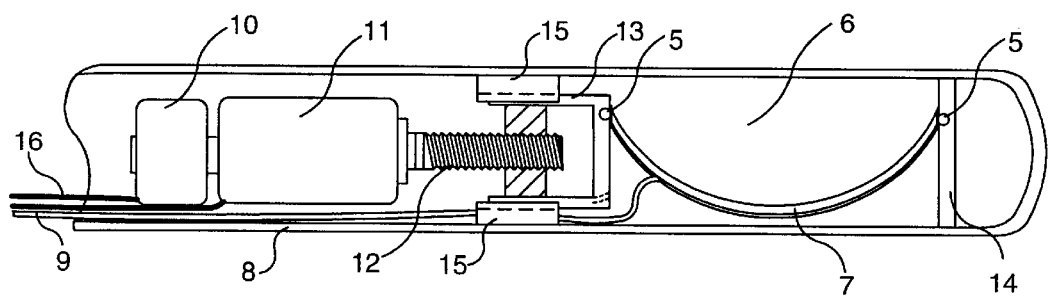

Any readily obtainable linear actuator may be used to vary the focal position, for example, between F and F' as shown, by rotating threaded shaft 1 and varying the radius of curvature of flexible transducer assembly 7. FIG. 13B illustrates an ultrasound applicator 52 that includes a small motor 11 that rotates a threaded shaft 12 within a threaded sliding shuttle 13. The threaded sliding shuttle is thus translated longitudinally by sliding within grooved slides 15. A rotational encoder 10 monitors the rotation of threaded shaft 12, producing signals that are output on a lead 16 and are indicative of the position of the threaded sliding shuttle, and thus, indicative of the radius of curvature of flexible transducer assembly 7.

Figure 13C:
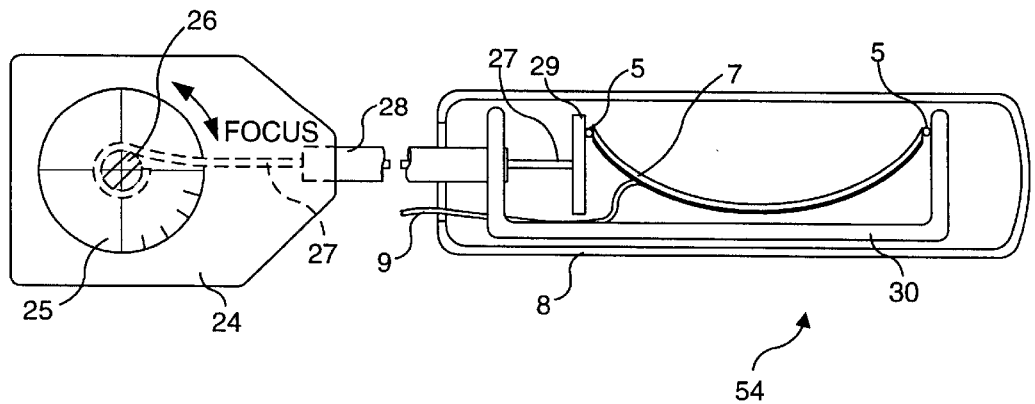

FIG. 13C depicts an ultrasound applicator 54, which is entirely manual, since focal depth is set by manually turning a knob 25 on an external control housing 24. A flexible cable 27 is retracted or extended relative to a fixed sheath 28 as knob 25 is rotated about a central hub 26. Flexible cable 27 extends inside housing 8 and is coupled to a moving movable member 29. As knob 25 is rotated, flexible cable 27 is either wound onto central hub 26, or is unwound from the hub. The longitudinal movement of flexible cable 27 pushes or pulls movable member 29. The flexible transducer assembly is supported between rods 5, one of which is connected to the movable member. The rod at the opposite end of the flexible transducer assembly is connected to a generally "U-shaped" bracket 30, which also supports an end of fixed sheath 28. The longitudinal translation of movable member 29 causes the radius of curvature and focal point of flexible transducer assembly 7 to change accordingly. Lead 9 conveys signals between the flexible transducer array and a control system (not shown).

Figure 13D:
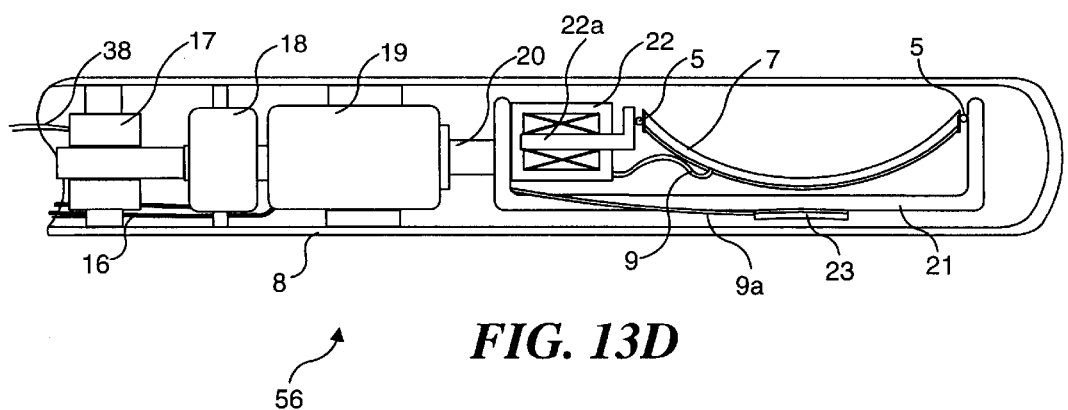

FIG. 13D adds additional complexity and capability in an ultrasound applicator 56, by permitting substantially full rotational motion of a rotatable carriage 21 that supports both a flexible transducer assembly 7 and a separate imaging transducer 23. One end of flexible transducer assembly 7 is coupled to support rod 5, which is affixed to rotatable carriage 21 and the opposite end is connected through support rod 5 to a movable solenoid member 22a. Imaging transducer 23 is mounted on the opposite side of rotatable carriage 21 from flexible transducer assembly 7, so that as the carriage rotates, the imaging transducer can be positioned to image a lesion or other prospective treatment site. A cable 9a is coupled to the imaging transducer and a commutator 17 that is coupled to cables 9 and 9a provides rotary electrical connections that convey signals between the transducers and a control system (not shown) through a lead 38. A solenoid assembly 22 provides linear actuation to vary the radius of curvature of flexible transducer 7, The solenoid assembly when actuated with an electrical current, magnetically translates movable solenoid member 22a longitudinally. Movable solenoid member 22a is coupled to support rod 5, which is connected to one end of the flexible transducer, as noted above. Electrical motor 19 is actuated to rotate a shaft 20 that is connected to rotatable carriage 21. Selective actuation of electrical motor 19 with electrical current provided through a lead 16 thus permits imaging transducer 23 or flexible transducer assembly 7 to be directed toward a desired region in a patient's body. Use of separate, dedicated imaging transducer 23 for imaging provides very high quality images that are co-aligned with the position of therapeutic ultrasound energy delivered from flexible transducer assembly 7. A rotational encoder 18 monitors the rotational position of shaft 20, producing an output signal over lead 16 that is indicative of the angular position of the rotatable carriage and thus, indicative of the direction in which flexible transducer assembly 7 and imaging transducer 23 are facing.

Figure 14A:
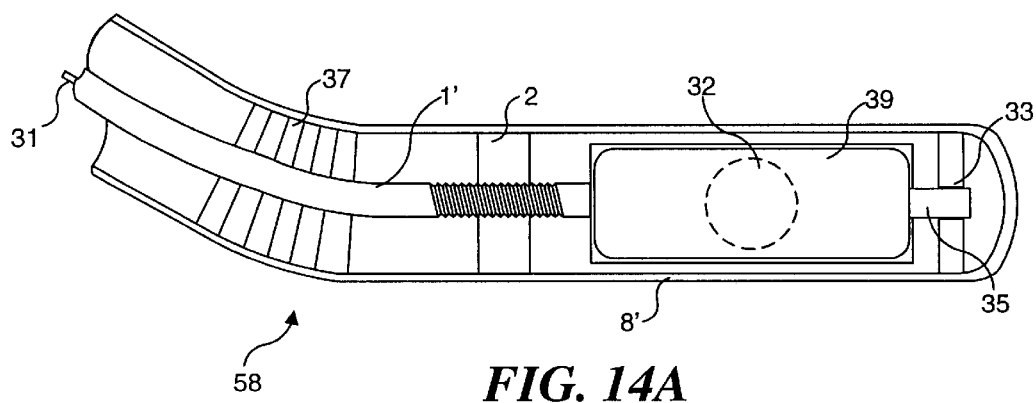
Figure 14B:
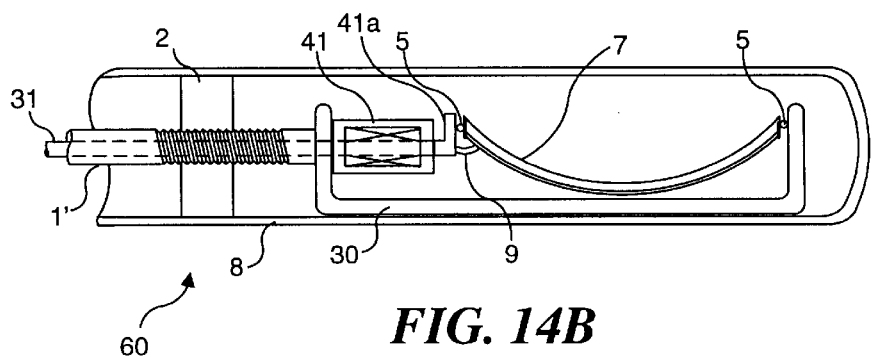
Figure 14C:
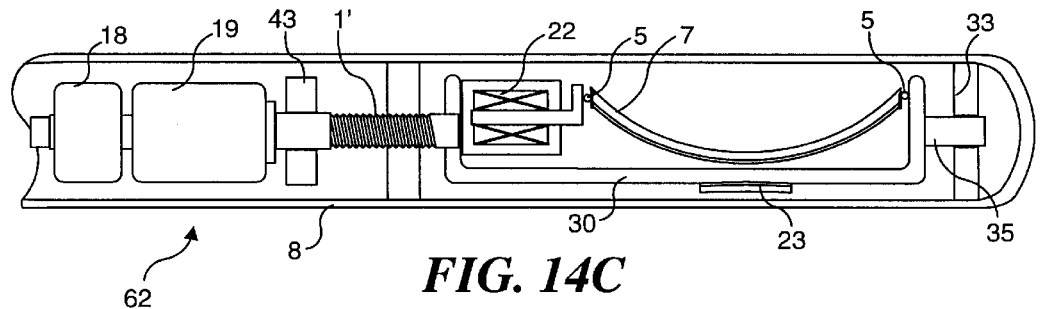

An applicator providing additional degrees of motion is shown in FIGS. 14A–14C. FIG. 14A shows an applicator 58 having a rotatably driven flexible threaded shaft 1' that translates a transducer assembly 39 along the longitudinal axis of the applicator as the flexible threaded shaft rotates within fixed turning block 2, moving the distal end 35 of the transducer assembly within a sliding pillow block 33, which prevents the transducer assembly from rotating. Applicator 58 has a housing 8' that includes a flexible section 37. A lead 31 that extends through the flexible threaded shaft conveys signals between the transducer assembly and an external control system (not shown). Transducer assembly 39 may optionally include a central imaging transducer 32 and can be fabricated as a single flexible transducer element or as a flexible array of transducer elements.

FIGS. 14B and 14C illustrate ultrasound applicators 60 and 62 that provide full, 3-D therapeutic coverage. In applicator 60, which is shown in FIG. 14B, this coverage is accomplished by combining the selective rotation of carriage 30 with longitudinal translation of the carriage using flexible threaded shaft 1', and solenoid assembly 41 to selectively control the radius of curvature of flexible transducer assembly 7. Flexible threaded shaft 1' both rotates to control a direction in which the flexible transducer assembly is facing and to control its longitudinal position within housing 8. Solenoid assembly 41 (or other suitable type of linear motor or linear actuator) is energized to longitudinally move movable solenoid member 41a, which is connected to support rod 5 to which the flexible transducer assembly is connected. The solenoid assembly thus controls the flexure of the flexible transducer assembly, which determines its focal point.

In FIG. 14C, applicator 62 includes electrical motor 19, rotational encoder 18, and commutator 43, eliminating the need for a long flexible drive shaft coupled to a remote drive. Electrical motor 19 drives threaded shaft 1, which rotates rotatable carriage 30 so that flexible transducer assembly 7 or imaging transducer 23 are directed toward a region of interest within a patient's body, and with continued rotation, can translate the rotatable carriage longitudinally within housing 8. Solenoid assembly 22 controls the radius of curvature of the flexible transducer assembly, as described above.

Figure 15A:
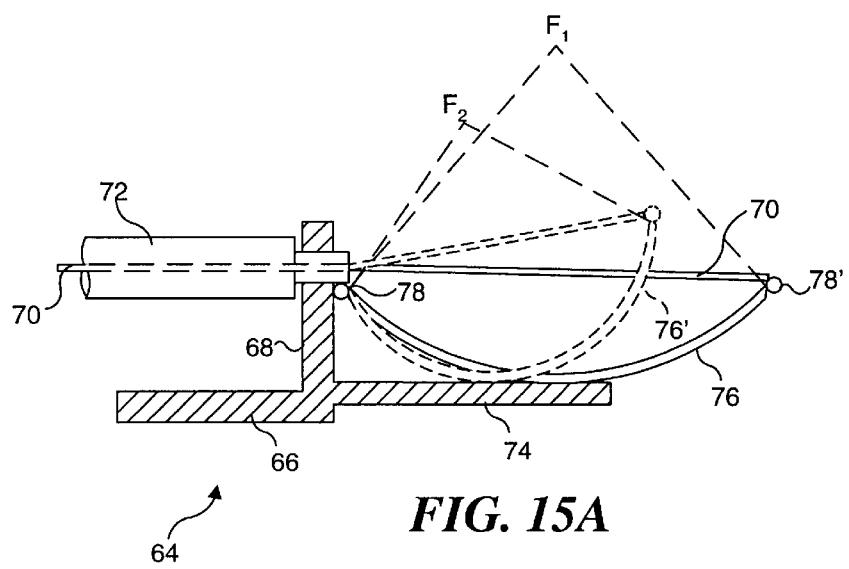
Figure 15B:
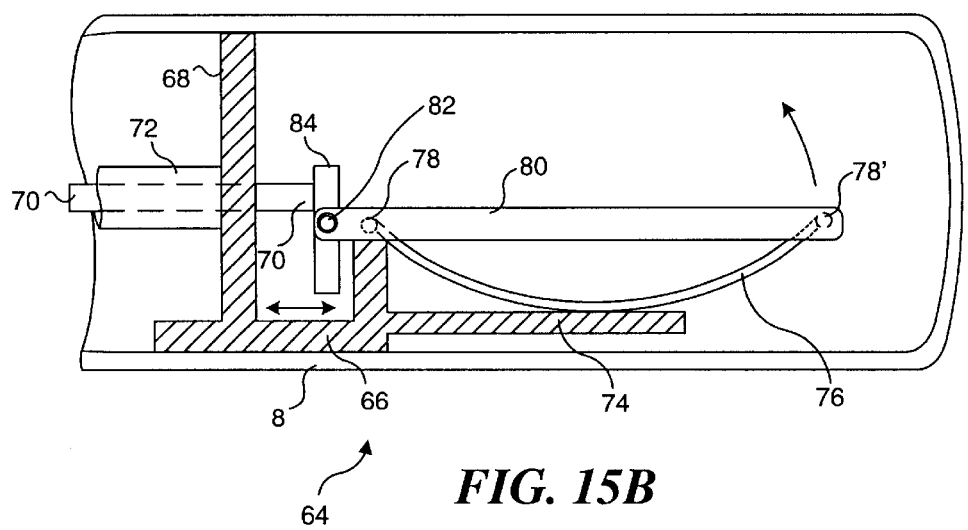

FIGS. 15A through 15C depict a bendable transducer assembly 64, in which a flexible array 76 is selectively and controllably bent away from a longitudinal axis of the device, thus providing for greater range of radii of curvature. Alternatively, a single flexible transducer element can be used instead of the array of elements. A large radius of curvature can thus be maintained when the probe is initially inserted into a trocar; and once inserted, smaller radii may be selected. Flexible array 76 is connected at an end 78 to an upright portion 68 of a supporting frame 66. A lateral shelf 74 provides a limit for flexible array 76 when it is focused at a focal point $F_1$, and subsequently, when it is focused at a closer focal point, $F_2$, which is offset to the left. To bend flexible array 76 so that it is configured as flexible array 76', a rod 70, which is attached to a distal end 78' of the flexible array, is drawn through a fixed sleeve 72. Fixed sleeve 72 is coupled to upright portion 68. Drawing rod 70 to the left (as shown in FIG. 15A) causes the flexible array or single transducer element to change shape and to curve more, producing a displaced and shorter focal point.

When bending the flexible array to properly focus the ultrasound beam, it is necessary to precisely know its geometry, i.e., its radius of curvature and the shape of the curvature. The shape of the curvature is preferably a segment of a circle. If so, the radius of the flexible array can be derived from the distance between its two ends. This distance can be precisely adjusted and maintained as discussed above.

It is much more difficult to maintain a desired curvature shape for a flexible array or flexible transducer that is a single element. When a force is applied to the two ends of a strip of array elements (or flexible transducer with only one element) having a uniform stiffness so as to move the ends toward each other, the resulting curvature of the strip is not a segment of a circle, but is instead, a segment of a hyperbolic or parabolic curve. One way to implement the simple compressing and stretching technique that is useful in shaping flexible array 76 in a desired curvature is to manufacture the flexible array so that it has a non-uniform stiffness. Specifically, the center of the flexible array should be stiffer than near its two ends. A proper stiffness function may be found experimentally in order to form a segment of circle. A non-uniform thickness in the supportive layer 157 of flexible array 191 may achieve this need. Supportive layer 157 is, however, also an acoustic matching layer of the transducer, and a matching layer having non-uniform thickness may not be acceptable from an acoustic standpoint. One solution is to bond one or two non-uniform stiffness metal pieces on the side of the array to create a stiffness profile meeting the requirement. Another solution is to make the housing of the transducer bendable and of non-uniform stiffness. In this embodiment, the flexible array and the housing are bent or flexed together, so that the non-uniform stiffness of the housing directly affects the curvature of the flexible array.

Another solution for controlling the array curvature is to employ position stops to constrain the array shape during bending. This technique is especially useful when only several predetermined radii of curvature are required. In FIG. 16A, a plurality of stop pins 221 are placed behind flexible array 191. Again, a flexible transducer that has only a single element can be used instead of the flexible array. The position of heads 222 of these stop pins that contact the back of flexible array 191 can be controlled mechanically to define a predetermined stop profile. When two ends 213 of the array 191 are pressed toward each other, the back of the array moves against heads 222 of the stop pins 221, which are positioned so that the shape of the array matches to the desired profile. For different array radii, the stop pins are set to different positions.

The arrangement of the stop pins also makes possible an arrangement for adjusting the curvature of the array either before the transducer is inserted into a patient, or after the transducer is in place. Notice that stop pins 221 have a configuration similar to that found in the pins of a conventional cylinder lock. Consequently, if the pins are mounted so that they move longitudinally to position heads 222, then ridges 215 of a key 209 inserted into a slot 207 in the transducer housing can act on the inner ends of the stops to set the desired position of the heads. The extension or depth of each ridge 215 on the key then determines how far the respective pin acted upon by the ridge is pushed, thereby controlling the position of the pin's head. Different keys having ridges of different depths can thus be used to achieve other curvature shapes for the flexible array. The user would simply insert the proper key to cause the desired curvature of flexible array 191 needed for a specific application of the transducer. While not shown in the drawings, it is also contemplated that a single key on which the ridges are shaped as cams having a variable depth could alternatively be used, so that depending on the angular position of this key in the slot of the transducer housing, a desired curvature shape could be "dialed" in before insertion of the transducer into the patient's body. If this option is used to control the pin positions, the key and transducer housing will be provided with predefined registration markings to enable the user to identify the shape that has been selected.

In FIG. 16B, a stop template 223 is disposed behind flexible array 191 (or behind a flexible transducer having only one element). Stop template 223 presses against the back surface of flexible array 191 to define a precise radius of curvature. Templates of different curvatures can be employed to define different radii of curvature.

The pin/key arrangement may be used to adjust the shape of flexible array even when the flexible array is disposed within a patient' body. As shown in FIG. 16C, this function can be achieved by providing a plurality of linear actuators 199 that are each separately controlled in response to signals supplied through leads 200. The linear actuators are mounted in a supporting frame 195 that includes a slot 197 to compressively hold the linear actuators. A remotely actuated shaft 193 acts on support rod 5 attached to one end of flexible array 191, providing a force that deforms the flexible array. The opposite end of the flexible array is pivotally attached to supporting frame 195. Signals supplied through leads 200 thus determine the depth of each pin 221 and control the curvature of flexible array 191, enabling an operator to readily change the curvature after the flexible array in an ultrasound applicator has been inserted into the body of a patient.

Mechanically Steered Array

To simplify a flexible array and its control system, it is desirable to use a smaller number of array elements 102. For a given array size, using fewer elements will require that the array element size be larger. As shown in FIGS. 2A and 2B, a larger array element has a narrower directivity pattern 123. To achieve a high intensity at the focus of an ultrasound therapy that is being administered, the narrow directivity patterns from all elements must be steered toward focus 132. However, steering of the array elements cannot normally be accomplished electronically. The present invention therefore provides a mechanically steered array to solve the problem and has the capability to focus at different depths, as shown in FIGS. 17A–17D and to shift the focus to different locations, as shown in FIGS. 18A and 18B.

The mechanical array comprises a plurality of small single-element transducers 232. Each ultrasound transducer 232 can pivot left and right on a shaft 233. The directivity pattern of the single element transducer is perpendicular to its center surface. The single element transducer has a concave surface 234 that focuses the ultrasound to the maximum focal depth of the array device. During ultrasound therapy, all of the small transducer elements are pivoted about their central axes so that their directivity patterns 123 are directed toward focus 132. Phase delays of the driving signals applied to energize the transducer elements are adjusted between $-\pi$ and $+\pi$ to ensure that the wave fronts from all transducer elements arrive at focus 132 in phase, so that the intensity at the focus is maximized. During ultrasound imaging, each small transducer element is used to scan its FOV and form an image frame. Images from all transducer elements can be spatially compounded (averaged) together to improve the image quality of the overall array.

Rotation or pivoting of the mechanical array elements can be implemented by using micro-electric motors or actuators 235, which are coupled to the transducer elements through linkage 239 comprising gears 247 and 249. Details of the drive and linkage assembly are shown for one transducer array element in FIG. 17D. As shown in this Figure, each micro-electric motor 235 rotatingly drives a shaft 243 on which is mounted gear 247. Gear 247 engages and rotates gear 249, which is attached to shaft 233. Rotation of shaft 233 rotates the transducer element. A rotational encoder 245 produces a signal indicative of the angular rotation of the transducer element, enabling the angular position of each transducer element to readily be determined. Because these elements only pivot left and right through a relatively small angle (typically less than 90°), a transducer signal wire 237 can be connected to the transducer element directly without the need to employ a brush, commutator, or other coupling device. The overall profile of an array 231 is also relatively small, so that it can be used in area where space is limited. Using only a few transducer elements 232 and their electronic controls, this mechanical array can be employed to scan a wide area for both imaging and therapy.

A configuration of control system modules for use with the present invention is shown in FIG. 19. Transducer elements 302 (shown numbered 1–N), each comprising a piezoelectric material are disposed in a curved array 344, corresponding to any of the curved array transducer embodiments discussed above. Elements 302 are connected to specific excitation and signal processing functional modules through therapy/imaging (T/I) switches 318 and transmit/receive (T/R) switches 334. Each element 302 in array 344 is electrically excited with a signal having predetermined frequency, amplitude, and phase characteristics to generate a composite phase pattern over the array so as to focus transmitted acoustic energy and locate the focal spot at a predetermined position. Note that in the above-described embodiments that do not employ phase differences for focusing and/or steering the ultrasound signal emitted by elements 302, the signals applied to the elements will be in phase. Also, it should be noted that elements 302 may be operated in a pulse-echo imaging mode to facilitate visualization of a target area or site in a patient's body.

FIG. 19 depicts a system embodying "N" separate piezoelectric elements and N corresponding complements of switches, matching networks, and signal processing functions, all variously under the control of a therapy control unit 308, an imaging control unit 310, and a multi-channel receiver 312.

A description of the interconnections and elements associated with one channel is instructive in understanding the overall function of all of the channels, which operate simultaneously in parallel. A channel numbered "1" in FIG. 19 will be described, and this description is equally applicable to the other channels. With T/I switch 318 of channel 1 in the "therapy" position, element 302 in that channel is connected to therapy matching network 320 in channel 1, which has characteristics such that this element will be substantially undamped. A programmable amplifier 316 in channel 1, which is under control of therapy control unit 308 sets a predetermined amplitude (which may be zero, if no excitation is to be applied to the element). A signal having a specific frequency and phase is provided to amplifier 316 in channel 1 by a programmable oscillator 314 in that channel, again under control of therapy control unit 308.

As T/I switch 318 in channel 1 selects the "imaging" position, element 302 is connected to an imaging matching network 322 in the channel, which has characteristics such that the element 300 is heavily damped. As shown in FIG. 19, in the receive mode, channel 1 imaging matching network 322 is connected to a transmit/receive (T/R) switch 334 in that channel, which selects either a connection to a pulser 332 for that channel when the imaging pulses are to be transmitted, or to the input for channel 1 of multi-channel receiver 312, when the echo pulses are to be received for imaging a site on a monitor 340. The pulse-echo imaging and display on monitor 340 is carried out in a manner well understood by those of ordinary skill in the diagnostic ultrasound art. In a similar manner, other elements 302 for channels 1 through N are connected to their respective switches and controlled processing chains.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. An ultrasound applicator that is capable of both ultrasound imaging and administering ultrasound therapy to a site, comprising:
   (a) a plurality of ultrasound transducer elements configured in an array and mounted in a housing;
   (b) a plurality of conductors adapted to couple a control system to the plurality of ultrasound transducer elements, for conveying signals that energize the plurality of ultrasound transducer elements in one of an imaging mode and a therapy mode; and
   (c) a quality factor circuit adapted to couple to the control system and connected to the plurality of ultrasound transducer elements, said quality factor circuit including a switch movable between a first position and a second position, the switch being selectively actuated into one of the first position and the second position to select a quality factor associated with the plurality of ultrasound transducer elements based upon whether the plurality of ultrasound transducer elements are operated in the imaging mode or the therapy mode, such that when the switch is in the first position, a bandwidth of each energized transducer is wider relative to a bandwidth of the energized transducer when the switch is in the second position.

2. The ultrasound applicator of claim 1, wherein the plurality of ultrasound transducer elements are configured in a concave array.

3. The ultrasound applicator of claim 2, wherein a focal point of the plurality of ultrasound transducer elements is determined by phase differences of the signals applied to energize the plurality of ultrasound transducer elements, said phase differences being controlled to achieve a desired focal point.

4. The ultrasound applicator of claim 2, wherein an ultrasound beam produced by the plurality of ultrasound transducer elements is steered in a desired direction based upon phase differences in the signals applied to energize the plurality of ultrasound transducer elements.

5. The ultrasound applicator of claim 2, wherein the plurality of ultrasound transducer elements comprise a flexible array mounted within the housing so that a radius of curvature of the flexible array is selectively variable to control a focal point of the flexible array.

6. The ultrasound applicator of claim 5, further comprising a movable shaft that is coupled to one end of the flexible array, said movable shaft being moved to vary the radius of curvature of the flexible array.

7. The ultrasound applicator of claim 5, further comprising a prime mover that is drivingly coupled to the movable shaft, said prime mover being selectively energized to move the movable shaft and thereby vary the radius of curvature of the flexible array and thus, vary the focal point of the flexible array.

8. The ultrasound applicator of claim 2, wherein the plurality of ultrasound transducer elements comprise a flexible array mounted within the housing, further comprising a movable link coupled to one end of the flexible array, said movable link being movable to control a curvature shape of the flexible array and thereby to control a direction in which an ultrasound beam is emitted by the flexible array.

9. The ultrasound applicator of claim 8, further comprising a limit that controls and limits the curvature shape assumed by the flexible array as the movable link is moved.

10. The ultrasound applicator of claim 1, wherein each of the plurality of ultrasound transducer elements comprises a composite mixture that includes a piezo-ceramic, an adhesive binder, and thermally conductive particles.

11. The ultrasound applicator of claim 1, further comprising a dampening network, such that when the switch is in the first position, the dampening network is coupled to each transducer, the dampening network providing a lower resistance that increases the bandwidth of each transducer.

12. The ultrasound applicator of claim 1, further comprising:
   (a) an imaging network that when coupled to each transducer achieves an impedance matched, highly damped transducer configuration, the imaging network being coupled to each transducer when the switch is in the first position; and
   (b) a therapy network that when coupled to each transducer achieves an impedance matched, weakly damped transducer configuration, the therapy network being coupled to each transducer when the switch is in the second position.

13. An ultrasound applicator that is capable of both ultrasound imaging and administering ultrasound therapy to a site, comprising:
   (a) a ultrasound transducer mounted in a housing;
   (b) a plurality of conductors adapted to couple a control system to the ultrasound transducer, for conveying signals that energize the ultrasound transducer in one of an imaging mode and a therapy mode; and
   (c) a quality factor circuit adapted to couple to the control system and connected to the ultrasound transducer, said quality factor circuit including a switch movable between a first position and a second position, the switch being selectively actuated in one of the first position and the second position to select a quality factor associated with the ultrasound transducer based upon whether the ultrasound transducer is operated in the imaging mode or the therapy mode, such that when the switch is in the first position, a bandwidth of the energized transducer is wider relative to a bandwidth of the transducer when the switch is in the second position.

14. The ultrasound applicator of claim 13, wherein the ultrasound transducer is configured in a concave curved shape.

15. The ultrasound applicator of claim 13, wherein the ultrasound transducer comprises a composite mixture that is flexible and includes a piezo-ceramic, an adhesive binder, and thermally conductive particles.

16. The ultrasound applicator of claim 15, wherein the ultrasound transducer is mounted within the housing so that a radius of curvature of the ultrasound transducer is selectively variable to control a focal point of ultrasound transducer.

17. The ultrasound applicator of claim 16, further comprising a movable shaft that is coupled to one end of the ultrasound transducer, said movable shaft being moved to vary the radius of curvature of the ultrasound transducer.

18. The ultrasound applicator of claim 17, further comprising a prime mover that is drivingly coupled to the movable shaft, said prime mover being selectively energized to move the movable shaft and thereby vary the radius of curvature of the ultrasound transducer and thus, vary the focal point of the ultrasound transducer.

19. The ultrasound applicator of claim 16, further comprising a movable link coupled to one end of the ultrasound transducer, said movable link being movable to control a curvature shape of the ultrasound transducer and thereby, to control a direction in which an ultrasound beam is emitted.

20. The ultrasound applicator of claim 19, further comprising a limit that controls and limits the curvature shape assumed by the ultrasound transducer as the movable link is moved.

21. The ultrasound applicator of claim 13, further comprising a dampening network, such that when the switch is in the first position the dampening network is coupled to the transducer, the dampening network providing a lower resistance that increases the bandwidth of the transducer.

22. The ultrasound applicator of claim 13, further comprising:
 (a) an imaging network that when coupled to the transducer achieves an impedance matched, highly damped transducer configuration, the imaging network being coupled to the transducer when the switch is in the first position; and
 (b) a therapy network that when coupled to the transducer achieves an impedance matched, weakly damped transducer configuration, the therapy network being coupled to the transducer when the switch is in the second position.

* * * * *